(12) United States Patent
St. Germain et al.

(10) Patent No.: US 8,652,192 B2
(45) Date of Patent: Feb. 18, 2014

(54) STENT AND SYSTEM AND METHOD FOR DEPLOYING A STENT

(75) Inventors: Jon St. Germain, Elk River, MN (US); Daniel O. Adams, Long Lake, MN (US)

(73) Assignee: St. Jude Medical, Cardiology Division, Inc., Minnetonka, MN (US)

( * ) Notice: Subject to any disclaimer, the term of this patent is extended or adjusted under 35 U.S.C. 154(b) by 1647 days.

(21) Appl. No.: 11/395,196

(22) Filed: Mar. 31, 2006

(65) Prior Publication Data

US 2007/0233232 A1 Oct. 4, 2007

(51) Int. Cl.
*A61F 2/06* (2013.01)

(52) U.S. Cl.
USPC .............................. 623/1.11; 623/1.1; 623/1.16

(58) Field of Classification Search
USPC ........ 623/1.11, 1.1, 1.15–1.19, 1.2, 1.36, 1.3; 606/108, 139, 151, 200, 194, 198
See application file for complete search history.

(56) References Cited

U.S. PATENT DOCUMENTS

| | | | |
|---|---|---|---|
| 5,360,401 A | 11/1994 | Turnland et al. | |
| 5,549,635 A | 8/1996 | Solar | |
| 5,591,223 A * | 1/1997 | Lock et al. | 623/1.17 |
| 5,607,466 A | 3/1997 | Imbert et al. | |
| 5,643,278 A | 7/1997 | Wijay | |
| 5,643,314 A | 7/1997 | Carpenter et al. | |
| 5,709,703 A | 1/1998 | Lukic et al. | |
| 5,725,571 A | 3/1998 | Imbert et al. | |
| 5,741,327 A * | 4/1998 | Frantzen | 623/1.34 |
| 5,843,090 A | 12/1998 | Schuetz | |
| 5,873,906 A * | 2/1999 | Lau et al. | 128/898 |
| 5,919,208 A * | 7/1999 | Valenti | 606/232 |
| 5,931,840 A * | 8/1999 | Goble et al. | 606/916 |
| 6,096,056 A | 8/2000 | Brown | |
| 6,120,522 A | 9/2000 | Vrba et al. | |
| 6,159,227 A | 12/2000 | Di Caprio et al. | |
| 6,179,878 B1 | 1/2001 | Duerig et al. | |
| 6,183,505 B1 | 2/2001 | Mohn, Jr. et al. | |
| 6,203,558 B1 | 3/2001 | Dubabek et al. | |
| 6,251,132 B1 | 6/2001 | Ravenscroft et al. | |
| 6,251,134 B1 * | 6/2001 | Alt et al. | 623/1.16 |
| 6,254,609 B1 | 7/2001 | Vrba et al. | |
| 6,280,412 B1 | 8/2001 | Pederson, Jr. et al. | |
| 6,350,277 B1 | 2/2002 | Kocur | |
| 6,425,898 B1 | 7/2002 | Wilson et al. | |
| 6,468,298 B1 | 10/2002 | Pelton | |
| 6,478,814 B2 | 11/2002 | Wang et al. | |
| 6,517,547 B1 | 2/2003 | Feeser et al. | |
| 6,530,947 B1 | 3/2003 | Eteneuer et al. | |
| 6,576,006 B2 | 6/2003 | Limon et al. | |
| 6,582,460 B1 | 6/2003 | Cryer | |

(Continued)

*Primary Examiner* — Corrine M McDermott
*Assistant Examiner* — Mark Mashack
(74) *Attorney, Agent, or Firm* — Holland & Hart

(57) ABSTRACT

The present invention is a vascular stent comprising a cylindrical wall radially expandable from a compressed state to an expanded state and including a plurality of cells. At least one cell includes a first primary member having a first restrainer member and a second primary member having a second restrainer member. When the cylindrical wall is in the expanded state, the first and second primary members are located a greater distance from each other than when the cylindrical wall is in the compressed state. The first and second restrainer members join to maintain the cylindrical wall in the compressed state. An expansion force applied to the cylindrical wall causes the first and second restrainer members to separate, thereby freeing the cylindrical wall to expand from the compressed state to the expanded state.

23 Claims, 9 Drawing Sheets

(56) References Cited

U.S. PATENT DOCUMENTS

| | | |
|---|---|---|
| 6,599,314 B2 * | 7/2003 | Mathis .......................... 623/1.11 |
| 6,613,077 B2 | 9/2003 | Gilligan et al. |
| 6,629,992 B2 | 10/2003 | Bigus et al. |
| 6,656,213 B2 | 12/2003 | Solem |
| 6,676,693 B1 | 1/2004 | Belding et al. |
| 6,814,746 B2 | 11/2004 | Thompson et al. |
| 6,893,458 B2 | 5/2005 | Cox et al. |
| 6,964,677 B2 * | 11/2005 | Osypka ......................... 623/1.11 |
| 7,022,132 B2 * | 4/2006 | Kocur .......................... 623/1.11 |
| 7,137,993 B2 * | 11/2006 | Acosta et al. ................ 623/1.11 |
| 7,175,654 B2 * | 2/2007 | Bonsignore et al. ......... 623/1.15 |
| 7,235,093 B2 * | 6/2007 | Gregorich ..................... 623/1.11 |
| 7,691,124 B2 * | 4/2010 | Balgobin ...................... 606/200 |
| 7,789,906 B2 * | 9/2010 | Blank ........................... 623/1.16 |
| 8,025,694 B2 * | 9/2011 | Strauss et al. ................ 623/1.16 |
| 8,486,132 B2 * | 7/2013 | Snow et al. .................. 623/1.16 |
| 2002/0111671 A1 * | 8/2002 | Stenzel ......................... 623/1.16 |
| 2002/0128706 A1 * | 9/2002 | Osypka ......................... 623/1.16 |
| 2002/0177890 A1 * | 11/2002 | Lenker ......................... 623/1.12 |
| 2002/0188343 A1 * | 12/2002 | Mathis .......................... 623/1.11 |
| 2003/0144725 A1 * | 7/2003 | Lombardi ..................... 623/1.13 |
| 2004/0015229 A1 * | 1/2004 | Fulkerson et al. ............ 623/1.22 |
| 2004/0236406 A1 * | 11/2004 | Gregorich ..................... 623/1.16 |
| 2005/0240184 A1 * | 10/2005 | Osman .......................... 606/61 |
| 2006/0069424 A1 * | 3/2006 | Acosta et al. ................ 623/1.12 |
| 2006/0195175 A1 * | 8/2006 | Bregulla ....................... 623/1.15 |

* cited by examiner

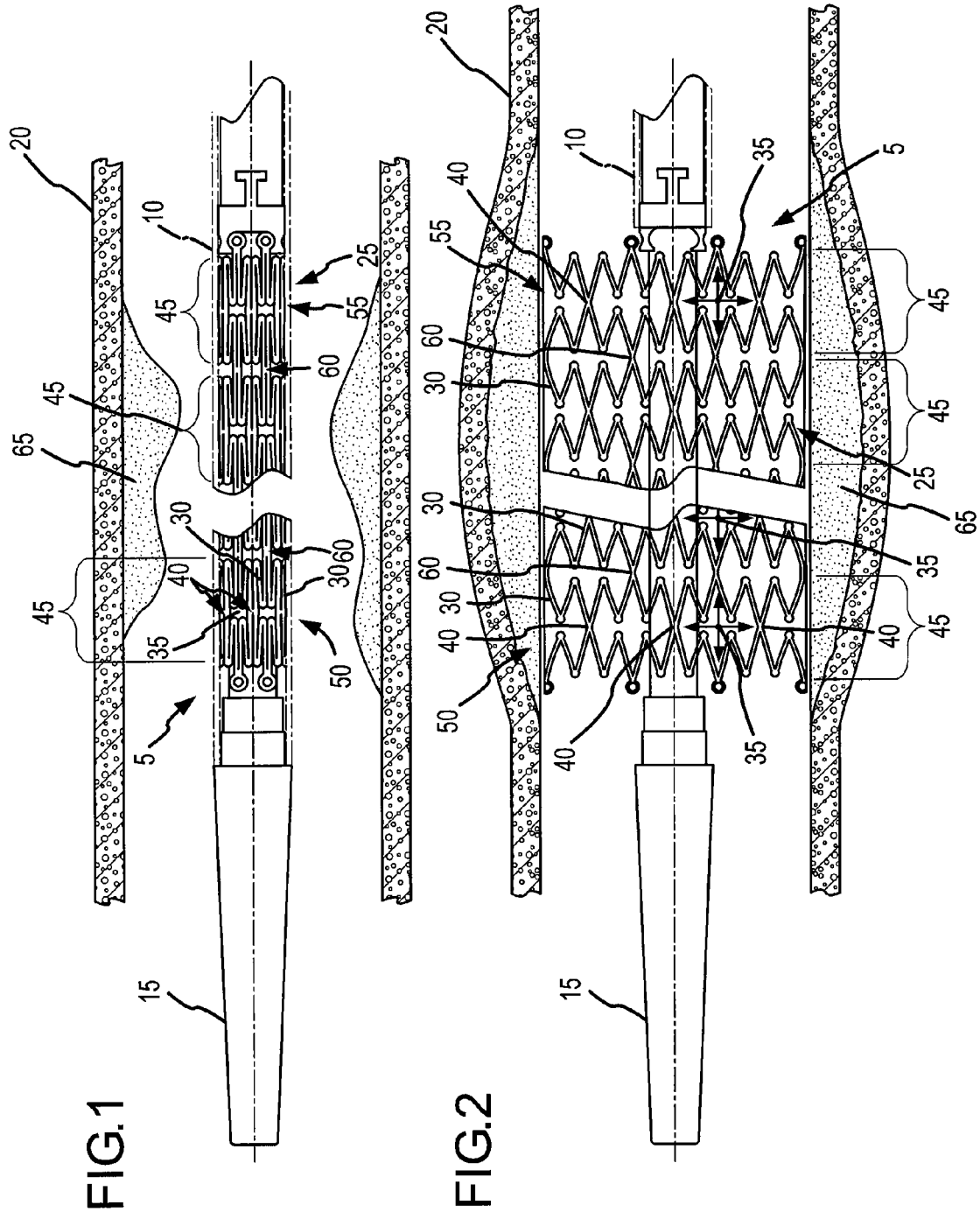

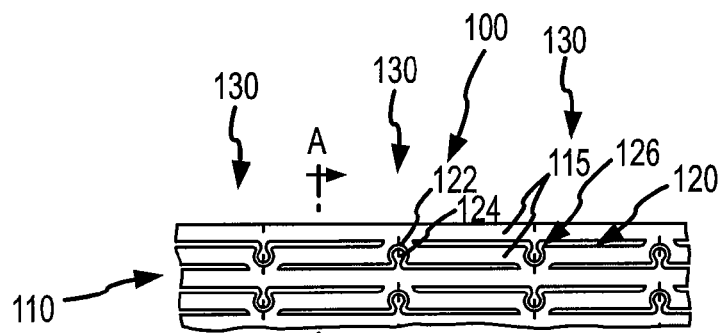
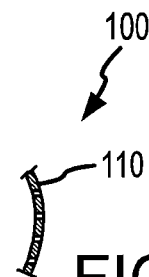
FIG.3a  FIG.3b
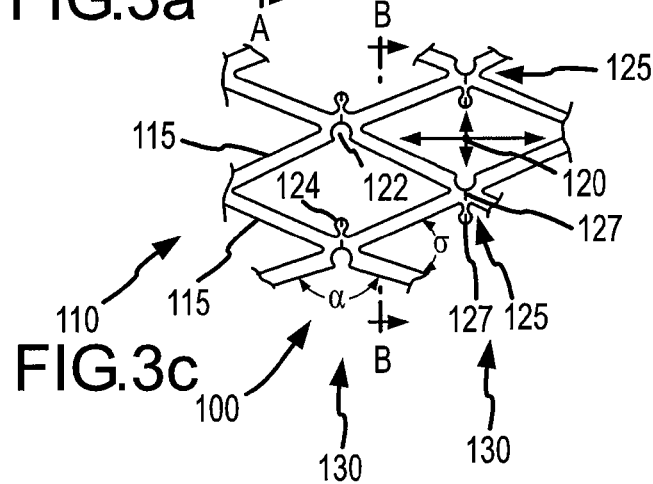
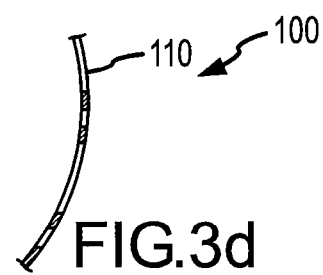
FIG.3c  FIG.3d
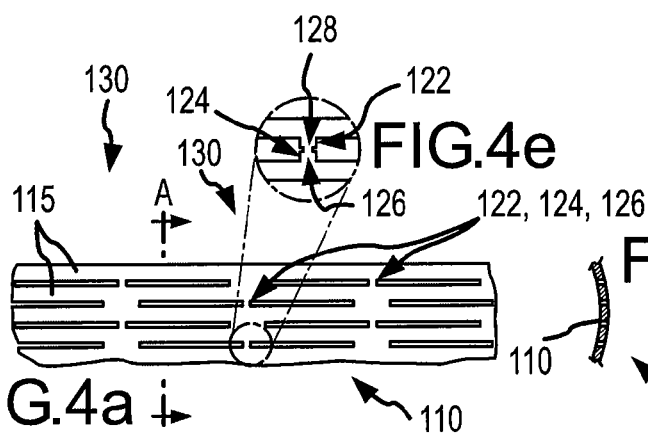
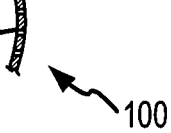
FIG.4a  FIG.4b  FIG.4e
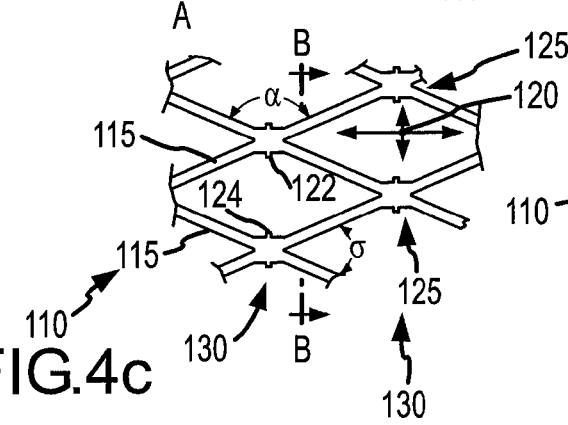
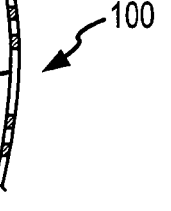
FIG.4c  FIG.4d

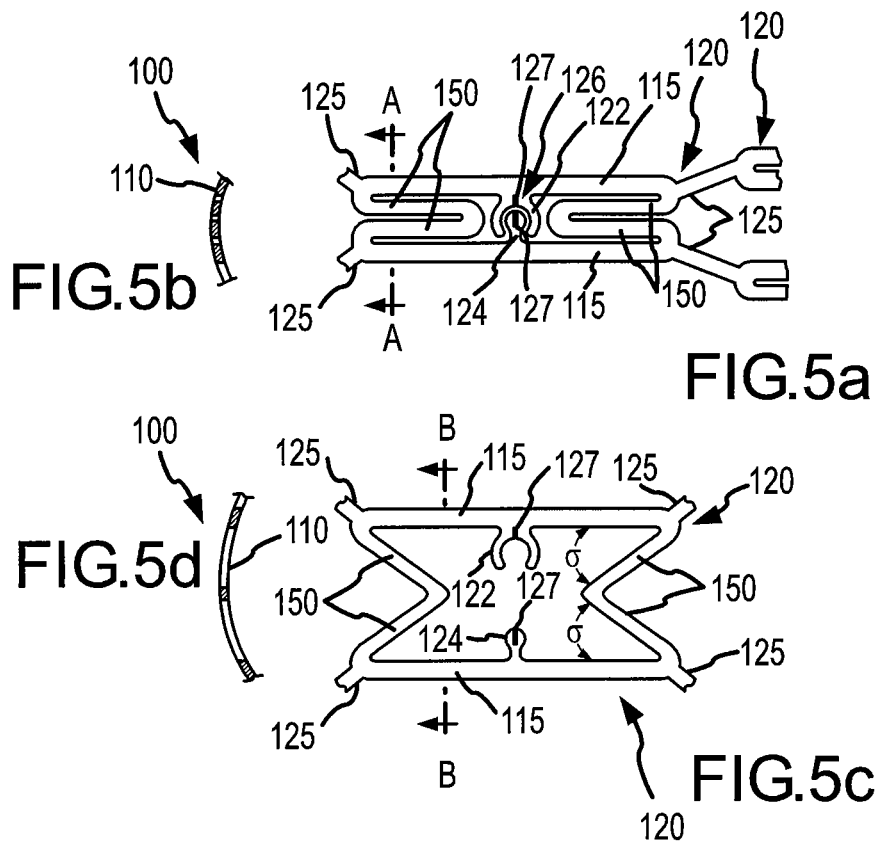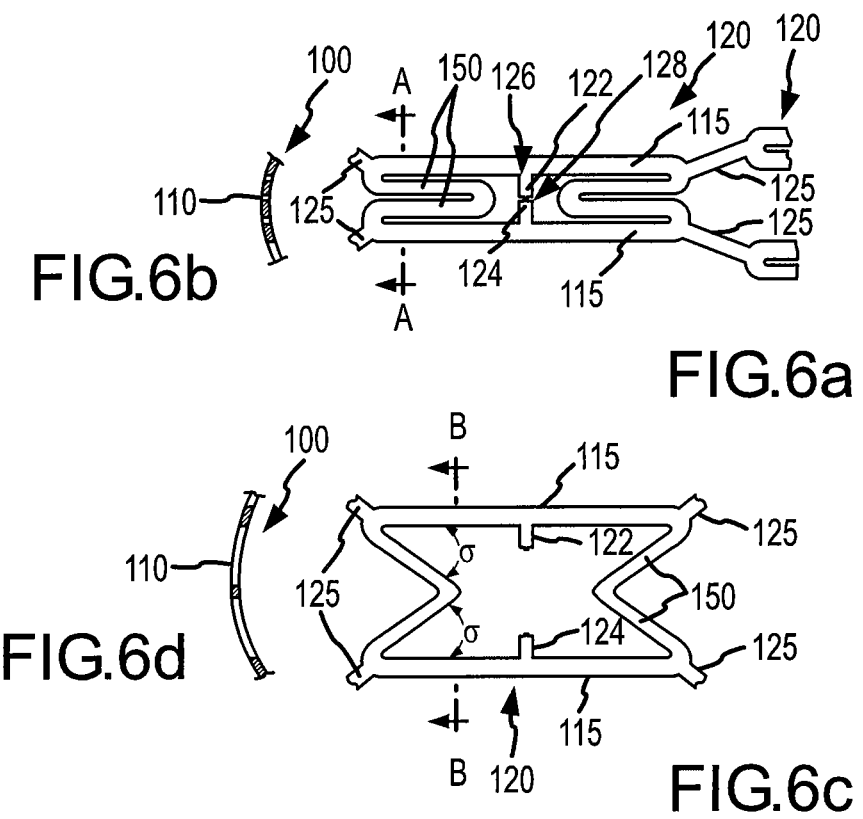

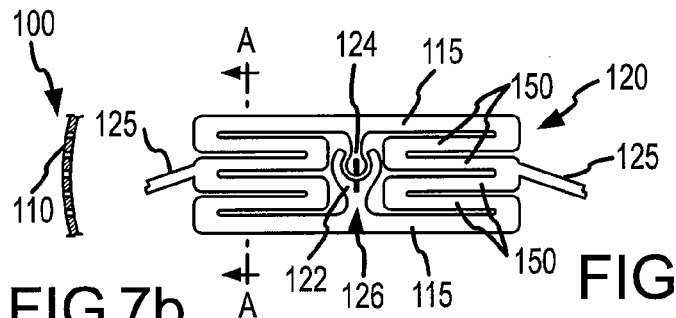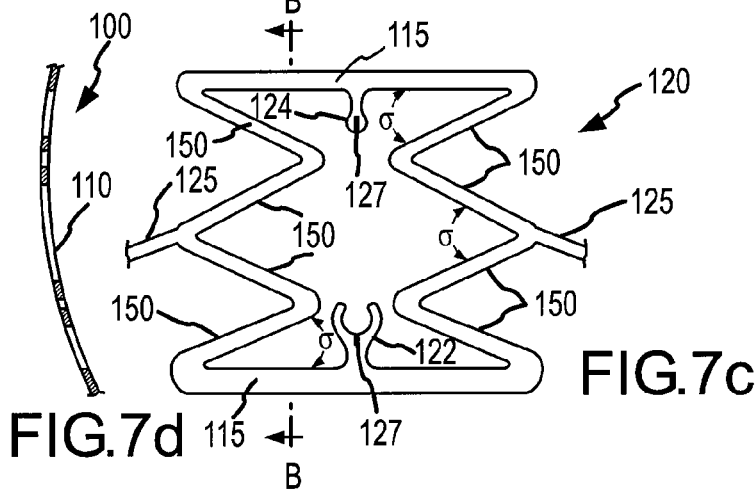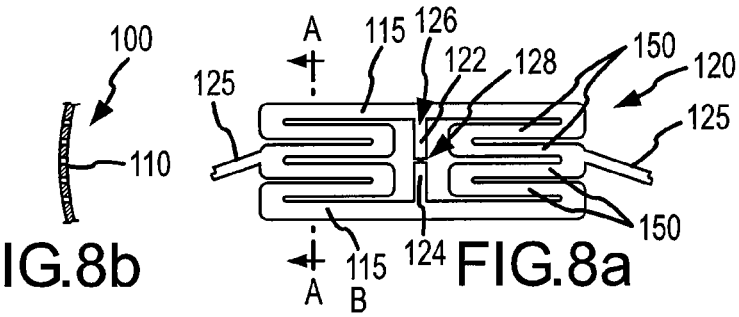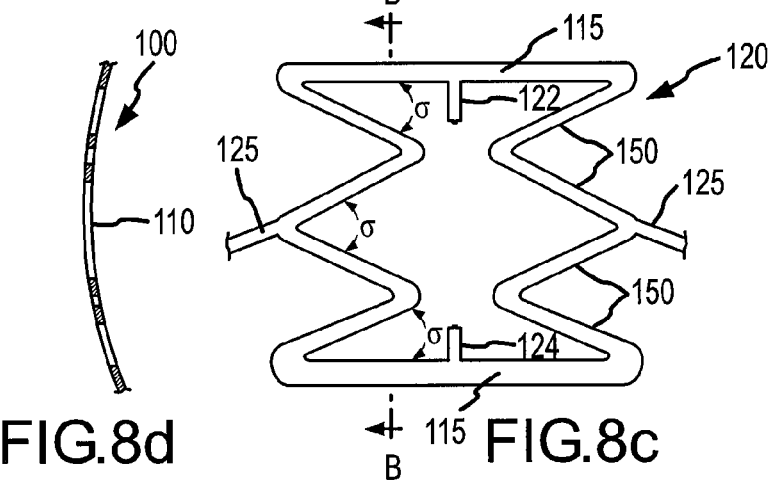

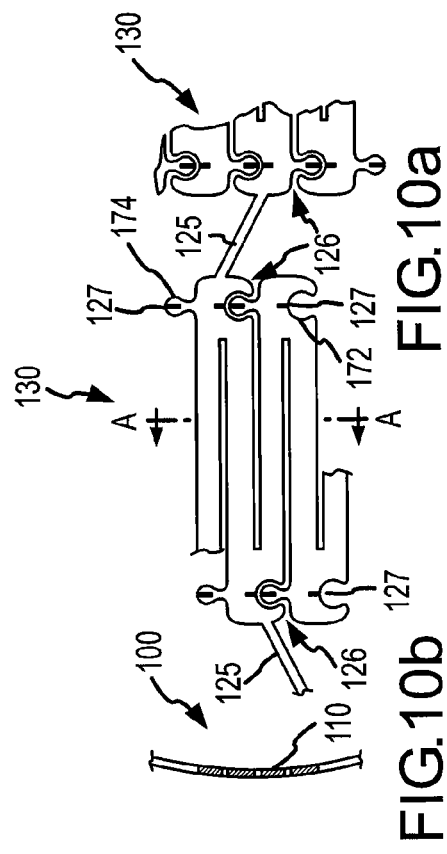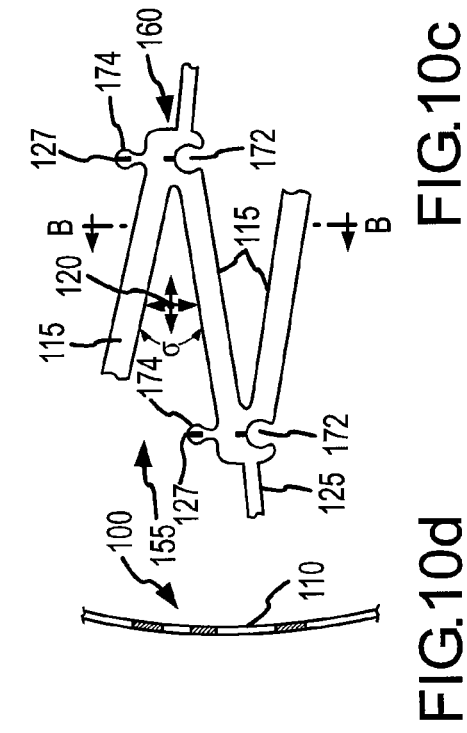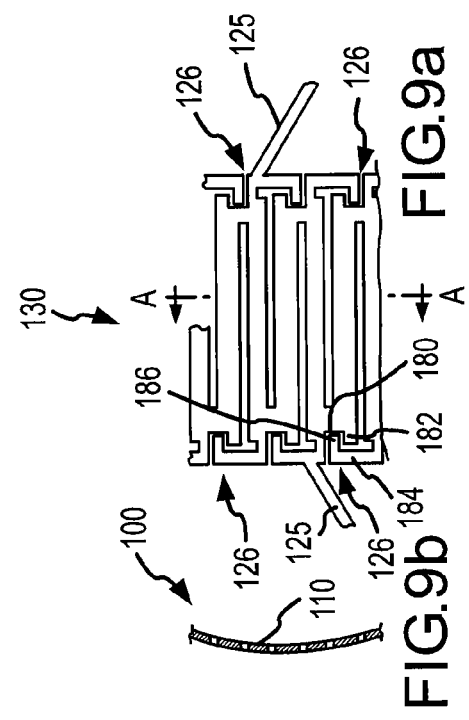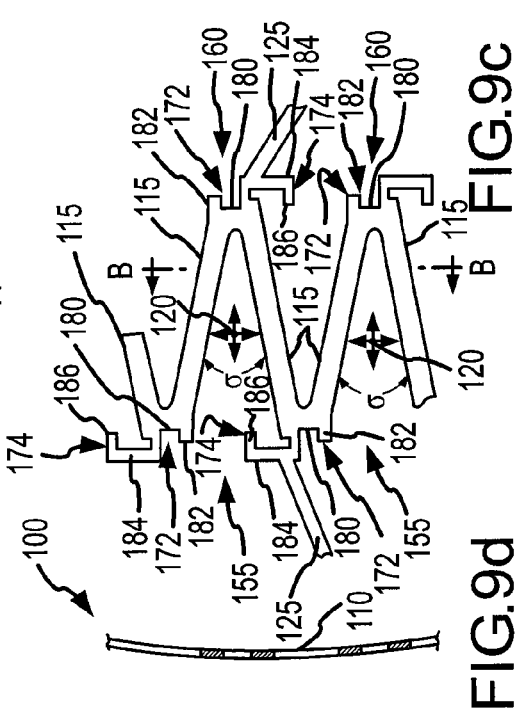

STENT AND SYSTEM AND METHOD FOR DEPLOYING A STENT

FIELD OF THE INVENTION

The present invention relates to expandable endoprosthesis devices (i.e., stents) and methods of deploying such devices. More specifically, the present invention relates to balloon expandable and self expanding stents and methods of deploying such devices that significantly improve device ease of use, lower the stent profile, improve catheter trackability and reduce the complications associated with stent deployment, including stent placement inaccuracy, the need for multiple device exchanges and the potential for distal embolization.

BACKGROUND OF THE INVENTION

Expandable endoprosthesis devices (i.e., stents) are adapted to be implanted into a patient's body lumen (e.g., a blood vessel) to maintain the patency thereof. There are two primary categories of stents, which are balloon expandable stents and self-expanding stents. Balloon expandable stents are made from materials (e.g. stainless steel, cobalt chromium alloys, etc.) and/or geometries that are plastically deformed by via the application of external forces against the balloon expandable stent (e.g., the expansion of the balloon against the stent). Once deformed, a balloon expandable stent maintains its plastically deformed state when the force is removed. Self-Expanding stents are made from materials (e.g. Nitinol, Algiloy, other shape memory alloys) and/or geometries (e.g., braided members, etc.) that are elastically deformed by external forces, but elastically return to their pre-deformed shape when the external force is removed.

Stents are particularly useful retaining vessel patency in the treatment and repair of blood vessels after a stenosis has been compressed by percutaneous transluminal coronary angioplasty (PTCA) or percutaneous transluminal angioplasty (PTA), or a stenosis has been removed by atherectomy or other means. Deploying a stent improves the results of the aforementioned procedures and reduces the possibility of restenosis.

In general, balloon expandable stent systems are the preferred method for treatment of intravascular stenosis. This is primarily driven by ease of use resulting from improved system flexibility, lower profile, better placement accuracy, etc. and inherent stent implant performance. preferred method of treatment due to the location of the stent implant. Specifically when stents are implanted in a location of the body (carotid artery, iliac artery, superficial femoral artery, etc.) where an external force may be applied to the implanted stent, it is necessary that, once the external force is removed, the stent return to its un-deformed (prior) shape in order to maintain lumen patency.

Stents are generally cylindrically shaped devices that function to hold open, and sometimes expand, a segment of a blood vessel or other arterial lumen (e.g., coronary or carotid arteries). Stents are usually delivered in a compressed condition to the target site and then deployed at that location into an expanded condition to support the vessel and help maintain it in an open position.

Stent delivery systems for balloon expandable stents typically include a tubular body (e.g., a catheter, sheath, etc.) having an inner guidewire lumen and a balloon extending over a distal portion of the tubular body. A balloon inflation lumen runs the length of the tubular body. The stent is compressed over the collapsed balloon. To help secure the stent in a compressed state about the balloon, it is often necessary to provide a retaining mechanism such as retaining structures under the balloon or over the stent ends (e.g., sleeves at each end of the stent). Such retaining mechanisms increase catheter bulk, stiffness and profile and decrease system trackability. Other retaining mechanisms known in the art include heat-treating the balloon to conform to the stent. U.S. Pat. Nos. 6,159,227, 6,096,056, 6,203,558 and 6,478,814 disclose various retaining mechanisms and are incorporated by reference herein in their entireties.

Stent delivery systems for implanting self-expandable stents typically include a tubular body (e.g., catheter, sheath, etc.) having an inner guidewire lumen, a compressed or collapsed stent mounted near the distal end of the tubular body, and an outer restraining sheath initially placed over the compressed stent prior to stent deployment. When the stent is to be deployed in the body vessel, the outer sheath is moved proximally to uncover the compressed stent. This allows the stent to move to its expanded condition.

Some self-expanding delivery systems utilize a push-pull technique in which the outer sheath is retracted while the inner tubular body is pushed forward. Still other systems use an actuating wire that is attached to the outer sheath. When the actuating wire is pulled to retract the outer sheath and deploy the stent, the inner tubular body remains stationary to prevent the stent from moving axially within the body vessel.

An example of a prior art self-expanding stent 5 is illustrated in FIGS. 1 and 2. FIG. 1 is a longitudinal elevation of the prior art self-expanding stent 5 in a compressed or non-deployed configuration as the stent 5 would appear within a retaining sheath 10 of a delivery system 15. FIG. 2 is a longitudinal elevation of the prior art self-expanding stent 5 of FIG. 1 in a fully deployed or expanded state as the stent 5 would appear within a body lumen 20 of a patient after the retaining sheath 10 of the delivery system 15 has been withdrawn to allow the stent 5 to deploy.

As can be understood from FIGS. 1 and 2, the self-expanding stent 5 has a cylindrical body 25, which radially expands substantially in diameter from the non-deployed state depicted in FIG. 1 to the deployed state depicted in FIG. 2. As indicated in FIGS. 1 and 2, the stent body 25 is formed from a plurality of adjacent inter-connected struts 30 arranged in a cellular pattern to form the outer circumferential surface of the stent 5. The body 25 is radially expandable. The cellular pattern of the inter-connected struts 30 forms cells 35. Each cell 35 joins with radially circumferentially adjacent cells 35 via cell interconnections 40 to form radially circumferentially continuous cell rings 45. With the exception of the most distal and proximal cell rings 50, 55, each cell ring 45 is sandwiched between, and joined to, its two longitudinally adjacent cell rings 45 via ring interconnections 60 to form a longitudinally continuous stent 5. The cell interconnections 40 align longitudinally and radially along the stent 5 with each other, and the ring interconnections 60 align longitudinally and radially along the stent 5 with each other. However, the cell and ring interconnections 40, 60 are longitudinally and radially offset from each other.

The stent 5 is retained in its compressed or non-deployed state, as depicted in FIG. 1, by a retaining sleeve or sheath 10 extending about the stent 5 when the stent 5 is being negotiated through a body lumen 20 of a patient. Upon reaching the stent implant location wherein plaque 65 is present, the sleeve 10 is withdrawn from about the stent 5, thereby freeing the stent 5 to expand to its fully expanded or deployed state, as depicted in FIG. 2. For further discussion regarding the exemplary self-expanding stent 5 of FIGS. 1 and 2, reference is made to U.S. Pat. No. 6,814,746, which issued Nov. 9, 2004, and is hereby incorporated by reference in its entirety.

Problems have been associated with the aforementioned delivery systems. For example, systems that rely on a push-pull design can experience movement of the collapsed stent within the body vessel when the inner tubular body is pushed forward. This can lead to inaccurate positioning and, in some instances, possible perforation of the vessel wall by a protruding end of the stent. Also, the thickness of the outer sheath adds to the delivery system profile and makes the system less trackable due to added tubular body stiffness.

Systems that utilize an actuating wire or full-length sheath design tend to move to shortcut the curvature of the anatomy of the patient due to increased stiffness of such systems. As the wire or sheath is pulled proximal, compression in the delivery system can cause the system to change position in the vasculature, leading to inaccurate stent placement.

Stent deployment systems that employ a restraining sheath have diameters that are large in comparison to stent delivery systems without a sheath. This is problematic when trying to deploy the stent in a body lumen having a reduced diameter. Sheaths and wires also add stiffness to the catheter, which inhibits tracking through the vasculature.

During deployment of a self-expanding stent using a proximally retractable sheath, the stent has a tendency to jump distally due to the expansion force from the distal end of the partially expanded stent acting against the restraint of the smaller diameter sheath end. This causes the stent to be displaced axially (distally) and contributes to inaccurate placement. Various restraint systems/methods have been contemplated to eliminate this axial movement. Examples include compressing the stent radially against friction surfaces, interlocking surfaces that project through stent openings, or tethers and wires that hold back the stent. Examples of such systems/methods are found in the following U.S. Pat. Nos. 6,582,460; 6,530,947; 6,517,547; 6,425,898; 6,254,609; 5,709,703; 5,607,466; 6,251,132; 6,350,277; 6,120,522; 6,814,746 and 6,576,006. These patents are incorporated herein by reference in their entireties.

To reduce the risk of distal embolization and possible neurological impairment from plaque disruption, distal embolization protection has become an essential component of stent deployment techniques in carotid arteries and bypass grafts. Current carotid artery stent deployment techniques require the following steps: placement of a distal embolic filter or proximal flow control protection system; pre-dilation of the stenosis (optional); deployment of the stent; post dilation of the deployed stent as needed; and removal of the embolic protection system. Such techniques are unnecessarily complicated because they require the insertion and withdrawal of multiple devices, increase case time, and increase the risk of stent misplacement and dislodgement by devices passing through the stent. In addition each catheter exchange introduces the possibility of plaque disruption and embolization, which could be missed by embolic protection systems, potentially increasing the risk for stroke, or flow restrictions in distal arteries. One example of an additional catheter exchange is the need to remove the stent delivery system following self-expanding stent deployment and the introduction of a separate balloon catheter to dilate the stent to its final diameter.

There have been attempts in the art to place a balloon on the same catheter as the self-expanding stent to eliminate a catheter exchange. U.S. Pat. No. 5,360,401, which issued Nov. 1, 1994 and is incorporated herein by reference in its entirety, describes a stent placed over a balloon with a protective pull back sheath over the stent. U.S. Pat. No. 5,843,090, which issued Dec. 1, 1998 and is incorporated herein by reference in its entirety, describes an uncovered balloon with a sheath bonded to it on the underside. The sheath restrains a stent placed under it in the compressed state. Both the balloon and sheath are retracted together to expose the self-expanding stent during deployment. After deployment the balloon and sheath are advanced through the stent and the stent post dilated. Although both of these concepts eliminate the exchange of the stent delivery system for a post dilatation balloon, both still utilize a sheath and require the pull back step. Furthermore, both have increased materials that add to the delivery profile and contribute to excess stiffness and poor trackability through the vasculature.

There is a need in the art for an improved expandable stent and a system for, and method of, deploying such a stent that offers improved ease of use, increased stent placement accuracy, lower delivered profile, and better trackability through the vasculature. There is also need for an improved expandable stent and a system for, and method of, deploying such a stent that offers a reduced number of catheter exchanges, thereby reducing the risk of plaque embolization, distal flow obstruction, and stroke.

BRIEF SUMMARY OF THE INVENTION

The present invention, in one embodiment, is a vascular stent comprising a cylindrical wall radially expandable from a compressed state to an expanded state and including a plurality of cells. At least one cell includes a first primary member having a first restrainer member and a second primary member having a second restrainer member. When the cylindrical wall is in the expanded state, the first and second primary members are located a greater distance from each other than when the cylindrical wall is in the compressed state. The first and second restrainer members join to maintain the cylindrical wall in the compressed state. An expansion force applied to the cylindrical wall causes the first and second restrainer members to separate, thereby freeing the cylindrical wall to expand from the compressed state to the expanded state.

The present invention, in one embodiment, is a system for deploying a vascular stent. The system comprises a catheter and a radially expandable stent. The catheter includes a balloon at a distal end of the catheter. The stent extends about the balloon and includes a plurality of integral restrainer members maintaining the stent in a collapsed state. Expanding the balloon causes the restrainer members to release, thereby allowing the stent to expand.

The present invention, in one embodiment, is a method of deploying a vascular stent via a balloon catheter in a treatment area of a body lumen. The method comprises positioning in the treatment area the stent in a collapsed state on a balloon of the catheter. The stent is maintained in the collapsed state via a plurality of restrainers integral to the stent. The restrainers are caused to separate by expanding the stent via balloon expansion.

The present invention, in one embodiment, is a method of treating a stenosis in a body lumen wherein pre-expansion of the stenosis is not required prior to stent deployment. The method comprises providing a stent mounted on a balloon of a catheter, retaining the stent in a compressed or non-deployed state about the balloon via a retaining member integral to the stent, positioning the stent within a stenosis without first pre-expanding the stenosis, and deploying the stent against the stenosis by expanding the balloon.

The present invention, in one embodiment, is a stent deploying system comprising a balloon catheter, an expandable stent and a means for restraining the stent in a collapsed state. The balloon catheter comprises a tubular body and a balloon coupled to the tubular body near a distal end of the tubular body. The expandable stent is located on the balloon.

The present invention, in one embodiment, is a stent deploying system comprising a balloon catheter and a vascular stent. The balloon catheter includes a tubular body and a balloon coupled to the tubular body near a distal end of the tubular body. The vascular stent is located on the balloon. The stent includes a restrainer member that acts to hold the stent in a collapsed state. When the balloon is caused to expand, the ability of the restrainer member to hold the stent in the collapsed state is overcome and the stent is free to expand.

The present invention, in one embodiment, is a radially expandable stent comprising a plurality of restrainer members that are integral to the stent and adapted to maintain the stent in a compressed state. The restrainer members on a first portion of the stent are adapted to fail or release prior to the restrainer members on a second portion of the stent.

The features, utilities, and advantages of various embodiments of the invention will be apparent from the following more particular description of embodiments of the invention as illustrated in the accompanying drawings and defined in the appended claims

BRIEF DESCRIPTION OF THE DRAWINGS

FIG. 1 is a longitudinal elevation of a prior art self-expanding stent in a compressed or non-deployed configuration as the stent would appear within a retaining sheath of a delivery system.

FIG. 2 is a longitudinal elevation of the prior art self-expanding stent of FIG. 1 in a fully deployed or expanded state as the stent would appear within a body lumen of a patient after the retaining sheath of the delivery system has been withdrawn to allow the stent to deploy.

FIG. 3a is an enlarged planar view of a portion of a cylindrical stent, wherein the stent is in a compressed or non-deployed state similar to the compressed or non-deployed state depicted in FIG. 1.

FIG. 3b is a cross-section through the portion of the cylindrical stent, as taken along section line A in FIG. 3a.

FIG. 3c is the same view of stent as depicted in FIG. 3a, except the stent is in a fully expanded or deployed state similar to the expanded or deployed state depicted in FIG. 2.

FIG. 3d is a cross-section through the portion of the cylindrical stent, as taken along section line B in FIG. 3c.

FIG. 4a is an enlarged planar view of a portion of a cylindrical stent, wherein the stent is in a compressed or non-deployed state similar to the compressed or non-deployed state depicted in FIG. 1.

FIG. 4b is a cross-section through the portion of the cylindrical stent, as taken along section line A in FIG. 4a.

FIG. 4c is the same view of stent as depicted in FIG. 4a, except the stent is in a fully expanded or deployed state similar to the expanded or deployed state depicted in FIG. 2.

FIG. 4d is a cross-section through the portion of the cylindrical stent, as taken along section line B in FIG. 4c.

FIG. 4e is an enlarged view of restrainer member utilized in the embodiment depicted in FIGS. 4a-4d.

FIG. 5a is an enlarged planar view of an individual cell of a cylindrical stent, wherein the stent is in a compressed or non-deployed state similar to the compressed or non-deployed state depicted in FIG. 1.

FIG. 5b is a cross-section through the portion of the cylindrical stent, as taken along section line A in FIG. 5a.

FIG. 5c is the same view of stent as depicted in FIG. 5a, except the stent is in a fully expanded or deployed state similar to the expanded or deployed state depicted in FIG. 2.

FIG. 5d is a cross-section through the portion of the cylindrical stent, as taken along section line B in FIG. 5c.

FIG. 6a is an enlarged planar view of an individual cell of a cylindrical stent, wherein the stent is in a compressed or non-deployed state similar to the compressed or non-deployed state depicted in FIG. 1.

FIG. 6b is a cross-section through the portion of the cylindrical stent, as taken along section line A in FIG. 6a.

FIG. 6c is the same view of stent as depicted in FIG. 6a, except the stent is in a fully expanded or deployed state similar to the expanded or deployed state depicted in FIG. 2.

FIG. 6d is a cross-section through the portion of the cylindrical stent, as taken along section line B in FIG. 6c.

FIG. 7a is an enlarged planar view of an individual cell of a cylindrical stent, wherein the stent is in a compressed or non-deployed state similar to the compressed or non-deployed state depicted in FIG. 1.

FIG. 7b is a cross-section through the portion of the cylindrical stent, as taken along section line A in FIG. 7a.

FIG. 7c is the same view of stent as depicted in FIG. 7a, except the stent is in a fully expanded or deployed state similar to the expanded or deployed state depicted in FIG. 2.

FIG. 7d is a cross-section through the portion of the cylindrical stent, as taken along section line B in FIG. 7c.

FIG. 8a is an enlarged planar view of an individual cell of a cylindrical stent, wherein the stent is in a compressed or non-deployed state similar to the compressed or non-deployed state depicted in FIG. 1.

FIG. 8b is a cross-section through the portion of the cylindrical stent, as taken along section line A in FIG. 8a.

FIG. 8c is the same view of stent as depicted in FIG. 8a, except the stent is in a fully expanded or deployed state similar to the expanded or deployed state depicted in FIG. 2.

FIG. 8d is a cross-section through the portion of the cylindrical stent, as taken along section line B in FIG. 8c.

FIG. 9a is an enlarged planar view of a portion of a cylindrical stent, wherein the stent is in a compressed or non-deployed state similar to the compressed or non-deployed state depicted in FIG. 1.

FIG. 9b is a cross-section through the portion of the cylindrical stent, as taken along section line A in FIG. 9a.

FIG. 9c is the same view of stent as depicted in FIG. 9a, except the stent is in a fully expanded or deployed state similar to the expanded or deployed state depicted in FIG. 2.

FIG. 9d is a cross-section through the portion of the cylindrical stent, as taken along section line B in FIG. 9c.

FIG. 10a is an enlarged planar view of a portion of a cylindrical stent, wherein the stent is in a compressed or non-deployed state similar to the compressed or non-deployed state depicted in FIG. 1.

FIG. 10b is a cross-section through the portion of the cylindrical stent, as taken along section line A in FIG. 10a.

FIG. 10c is the same view of stent as depicted in FIG. 10a, except the stent is in a fully expanded or deployed state similar to the expanded or deployed state depicted in FIG. 2.

FIG. 10d is a cross-section through the portion of the cylindrical stent, as taken along section line B in FIG. 10c.

DETAILED DESCRIPTION OF THE INVENTION

Figure 11B:
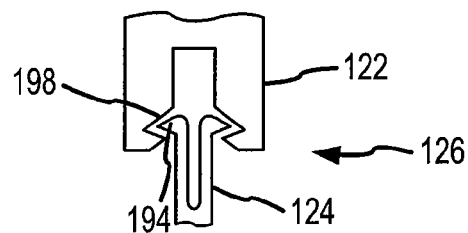
FIG. 11b is a side elevation of the male restrainer portion of FIG. 11a being received in the female restrainer portion.

The present invention, in one embodiment, is an expandable or self-expandable endoprosthesis device (i.e., a cylindrical vascular stent) that is at least initially deployed via a balloon catheter. As will be discussed in detail, in various embodiments, the stent includes at least one integral restrainer member that maintains the stent in a compressed or non-deployed state about the balloon of the balloon catheter until the balloon is expanded to overcome the restrainer member. Once the restrainer members are overcome by the expansion of the balloon, the stent is then free to self-expand or, alternatively, to be expanded via further expansion of the balloon.

As will be understood from the following discussion, the stent and its method of deployment are advantageous because they reduce delivery system profile and improve delivery system trackability and stent placement accuracy and control. With respect to self-expanding stents, the stent and its method of deployment eliminate the need for retractable sheaths and minimize the number of devices and steps needed to deploy the stent within a body lumen of a patient. For example, in one embodiment, the present invention allows self-expanding stent deployment and post dilation with the same balloon catheter and without catheter exchanges.

For a discussion of a first two embodiments of the cylindrical stent 100 of the present invention, reference is made to FIGS. 3a-3d and FIGS. 4a-4e. FIG. 3a is an enlarged planar view of a portion of a cylindrical stent 100, wherein the stent 100 is in a compressed or non-deployed state similar to the compressed or non-deployed state depicted in FIG. 1. FIG. 3b is a cross-section through the portion of the cylindrical stent 100, as taken along section line A in FIG. 3a. FIG. 3c is the same view of stent 100 as depicted in FIG. 3a, except the stent 100 is in a fully expanded or deployed state similar to the expanded or deployed state depicted in FIG. 2. FIG. 3d is a cross-section through the portion of the cylindrical stent 100, as taken along section line B in FIG. 3c. FIGS. 4a-4d are the same respective views as depicted in FIGS. 3a-3d, except of another embodiment of the stent 100. FIG. 4e is an enlarged view of a restrainer member utilized in the embodiment depicted in FIGS. 4a-4d.

Similar to the stent 5 depicted in FIGS. 1-2, the stents 100 of the subject invention depicted in FIGS. 3a-3d and 4a-4d each have a radially expandable cylindrical body defined by a cylindrical wall 110. As can be understood from FIGS. 3a-3d and 4a-4d, the radius of curvature of the cylindrical wall 110 increases substantially when the stent 100 expands from the compressed or non-deployed state, as depicted in FIGS. 3a-3b and 4a-4b, to the expanded or deployed state, as depicted in FIGS. 3c-3d and 4c-4d.

As indicated in FIGS. 3a, 3c, 4a and 4c, the stent wall 110 is formed from a plurality of adjacent inter-connected struts 115 arranged in a cellular pattern to form the outer circumferential surface of the stent 100. The cellular pattern of the inter-connected struts 115 forms cells 120. In other words, groups of struts 115 form or define cells 120 that open up or expand when the stent 100 expands from a compressed or non-deployed state, as shown in FIGS. 3a-3b and 4a-4b, to an expanded or deployed state, as shown in FIGS. 3c-3d and 4c-4d.

As illustrated in FIGS. 3a, 3c, 4a and 4c, each cell 120 includes an upper primary strut 115 and a lower primary strut 115. The two primary struts 115 are joined to each other at their respective ends. In one embodiment, as shown in FIGS. 3a, 3c, 4a and 4c, for each cell 120, a first restrainer portion 122 is located at the longitudinal center of the one primary strut 115, and a second restrainer portion 124 is located at the longitudinal center of the other primary strut 115.

As shown in FIG. 3A, in one embodiment, the restrainer portions 122, 124 mechanically engage each other form a restrainer 126 that maintains the associated primary struts 115 adjacent to each other, which thereby keeps the associated cell 120 compressed and the stent 100 in the non-deployed state. In one embodiment, one restrainer portion 122 is a female portion 122 for receiving a second restrainer portion 124, which is a male portion. As indicated in FIG. 3C, the restrainer portions 122, 124 can be disengaged from each other to allow the associated primary struts 115 to move away from each other, which allows the associated cell 120 to expand and the stent 100 to assume a deployed state. In one embodiment, the restrainer portions 122, 124 can be coupled or recoupled to each other, as well as decoupled. As shown in FIGS. 3A and 3C, in one embodiment, the female and male portions 122, 124 are rounded and include slots 127 to assist the restrainer portions 122, 124 in deforming while coupling together or decoupling.

As shown in FIGS. 4a and 4e, in one embodiment, the restrainer portions 122, 124 are bonded to each other to form a restrainer 126 that maintains the associated primary struts 115 adjacent each other, which thereby keeps the associated cell 120 compressed and the stent 100 in the non-deployed state. In one embodiment, the restrainer portions 122, 124 have a bond 128 that is formed via sonic welding, heat welding, chemical welding, or mechanical welding. Alternatively, in one embodiment, the bond 128 is an uninterrupted integral extension of one restrainer portion 122 to the other restrainer portion 124, thereby forming the restrainer 126. As indicated in FIG. 4c, the restrainer portions 122, 124 can be disengaged from each other by causing the bond 128 to fail, thereby allowing the associated primary struts 115 to move away from each other, which allows the associated cell 120 to expand and the stent 100 to assume a deployed state.

As can be understood from FIGS. 3a, 3c, 4a and 4c, each cell 120 joins with radially circumferentially adjacent cells 120 via interconnections 125 to form radially circumferentially continuous cell rings 130. With the exception of the most distal and proximal cell rings 130 of a stent 100, each cell ring 130 is sandwiched between, and joined to, its two longitudinally adjacent cell rings 130 via interconnections 125 to form a longitudinally continuous stent 100.

As shown in FIGS. 3a and 4a, when the stent 100 is in the compressed or non-deployed state, the struts 115 are positioned close to each other. More specifically, in one embodiment, when the stent 100 is in the compressed or non-deployed state, the struts 115 are oriented generally parallel to each other. As indicated in FIGS. 3b and 4b, when the stent 100 is in the compressed or non-deployed state, the radius of the curvature of the wall 110 is small.

As shown in FIGS. 3c and 4c, when the stent 100 is in the expanded or deployed state, the struts 115 are positioned away from each other. More specifically, in one embodiment, when the stent 100 is in the expanded or deployed state, the struts 115 are oriented oblique to each other. In one embodiment, when the stent 100 is in the expanded or deployed state, the primary struts 115 bend or deflect at their respective middles (e.g., at the location of their respective restrainer members 122, 124) forming an obtuse angle $\alpha$. At the same time, an acute angle $\sigma$ is formed between the joined ends of the primary struts 115 forming a cell 120. In one embodiment, as indicated in FIGS. 3d and 4d, when the stent 100 is in the compressed or non-deployed state, the radius of the curvature of the wall 110 is large.

For a discussion of four more embodiments of the cylindrical stent 100 of the subject invention, reference is made to FIGS. 5a-5d, 6a-6d, 7a-7d, and 8a-8d. FIG. 5a is an enlarged planar view of an individual cell 120 of a cylindrical stent 100, wherein the stent 100 is in a compressed or non-deployed state similar to the compressed or non-deployed state depicted in FIG. 1. FIG. 5b is a cross-section through the portion of the cylindrical stent 100, as taken along section line A in FIG. 5a. FIG. 5c is the same view of stent 100 as depicted in FIG. 5a, except the stent 100 is in a fully expanded or deployed state similar to the expanded or deployed state depicted in FIG. 2. FIG. 5d is a cross-section through the portion of the cylindrical stent 100, as taken along section line B in FIG. 5c. FIGS. 6a-6d are the same respective views as depicted in FIGS. 5a-5d, except of another embodiment of the stent 100. FIGS. 7a-7d are the same respective views as depicted in FIGS. 5a-5d, except of another embodiment of the stent 100. FIGS. 8a-8d are the same respective views as depicted in FIGS. 5a-5d, except of another embodiment of the stent 100.

The cells 120 depicted in FIGS. 5a-8d combine with similar cells 120 to form a stent wall 110 in a manner generally the same as discussed above with respect to FIGS. 3a-4d. In other words, the cells 120 of FIGS. 5a-8d interconnect with adjacent cells 120 via interconnections 125 to form cell rings 130 that interconnect with adjacent cell rings 130 to form the stent wall 110. As a result, the cell walls 110 employing the cells 120 depicted in FIGS. 5a-8d are radially expandable from a compressed or non-deployed state, as shown in FIGS. 5a, 5b, 6a, 6b, 7a, 7b, 8a and 8b, to an expanded or deployed state, as depicted in FIGS. 5c, 5d, 6c, 6d, 7c, 7d, 8c and 8d.

In one embodiment, as can be understood from FIGS. 5a-8d, each cell 120 includes an upper primary member or strut 115 and a lower primary member or strut 115. The two primary struts 115 are joined to each other at their respective ends via groups of intermediate members or struts 150 that extend between the primary struts 115 in a serpentine manner. In one embodiment, as shown in FIGS. 5a-6d, each group of intermediate struts 150 includes a single pair of intermediate struts 150. In one embodiment, as shown in FIGS. 7a-8d, each group of intermediate struts 150 includes two pairs of intermediate struts 150. In one embodiment, as shown in FIGS. 5a, 5c, 6a, 6c, 7a, 7c, 8a and 8c, for each cell 120, a first restrainer portion 122 is located at the longitudinal center of the one primary strut 115, and a second restrainer portion 124 is located at the longitudinal center of the other primary strut 115.

As shown in FIGS. 5a and 7a, in one embodiment, the restrainer portions 122, 124 mechanically engage each other to form a restrainer 126 that maintains the associated primary struts 115 and intermediate struts 150 adjacent each other, which thereby keeps the associated cell 120 compressed and the stent 100 in the non-deployed state. In one embodiment, one restrainer portion 122 is a female portion 122 for receiving a second restrainer portion 124, which is a male portion. As indicated in FIGS. 5c and 7c, the restrainer portions 122, 124 can be disengaged from each other to allow the associated primary struts 115 and intermediate struts 150 to move away from each other, which allows the associated cell 120 to expand and the stent 100 to assume a deployed state. In one embodiment, the restrainer portions 122, 124 can be coupled to each other and recoupled to each other, as well as decoupled. As shown in FIGS. 5a, 5c, 7a and 7c, in one embodiment, the female and male portions 122, 124 are rounded and include slots 127 to assist the restrainer portions 122, 124 in deforming while coupling together or decoupling.

As shown in FIGS. 6a, 6e, 8a and 8e, the restrainer portions 122, 124 are bonded to each other to form a restrainer 126 that maintains the associated primary struts 115 and intermediate struts 150 adjacent each other, which thereby keeps the associated cell 120 compressed and the stent 100 in the non-deployed state. In one embodiment, the restrainer portions 122, 124 have a bond 128 that is formed via sonic welding, heat welding, chemical welding, or mechanical welding. Alternatively, in one embodiment, the bond 128 is an uninterrupted integral extension of one restrainer portion 122 to the other restrainer portion 124, thereby forming the restrainer 126. As indicated in FIGS. 6c and 8c, the restrainer portions 122, 124 can be disengaged from each other by causing the bond 128 to fail, thereby allowing the associated primary struts 115 and intermediate struts 150 to move away from each other, which allows the associated cell 120 to expand and the stent 100 to assume a deployed state.

As shown in FIGS. 5a, 6a, 7a and 8a, when the stent 100 is in the compressed or non-deployed state, the struts 115, 150 are positioned close to each other. More specifically, in one embodiment, when the stent 100 is in the compressed or non-deployed state, the struts 115, 150 are oriented generally parallel to each other. As indicated in FIGS. 5b, 6b, 7b and 8b, when the stent 100 is in the compressed or non-deployed state, the radius of the curvature of the wall 110 is small.

As shown in FIGS. 5c, 6c, 7c and 8c, when the stent 100 is in the expanded or deployed state, the struts 115, 150 are positioned away from each other. More specifically, in one embodiment, when the stent 100 is in the expanded or deployed state, the primary struts 115 are displaced away from each other, but remain parallel to each other, and the intermediate struts 150 are displaced away from each other and are oriented oblique to each other and the primary struts 115. In one embodiment, when the stent 100 is in the expanded or deployed state, the primary struts 115 displace from each other, remain parallel to each other, and generally do not deflect along their respective lengths, and the intermediate struts 150 displace from each other to form an expanded serpentine shape with acute angles $\sigma$ between the pairs of intermediate struts 150 and the intermediate struts 150 and the primary struts 115. In one embodiment, as indicated in FIGS. 5d, 6d, 7d and 8d, when the stent 100 is in the compressed or non-deployed state, the radius of the curvature of the wall 110 is large.

For a discussion of two more embodiments of the cylindrical stent 100 of the subject invention, reference is made to FIGS. 9a-9d and 10a-10d. FIG. 9a is an enlarged planar view of a portion of a cylindrical stent 100, wherein the stent 100 is in a compressed or non-deployed state similar to the compressed or non-deployed state depicted in FIG. 1. FIG. 9b is a cross-section through the portion of the cylindrical stent 100, as taken along section line A in FIG. 9a. FIG. 9c is the same view of stent 100 as depicted in FIG. 9a, except the stent 100 is in a fully expanded or deployed state similar to the expanded or deployed state depicted in FIG. 2. FIG. 9d is a cross-section through the portion of the cylindrical stent 100, as taken along section line B in FIG. 9c. FIGS. 10a-10d are the same respective views as depicted in FIGS. 9a-9d, except of another embodiment of the stent 100.

The cells 120 depicted in FIGS. 9a-10d combine with similar cells 120 to form a stent wall 110 in a manner generally the same as discussed above with respect to FIGS. 3a-4d. In other words, the cells 120 of FIGS. 9a-10d interconnect with adjacent cells 120 via interconnections 125 to form cell rings 130 that interconnect with adjacent cell rings 130 to form the stent wall 110. As a result, the cell walls 110 employing the cells 120 depicted in FIGS. 9a-10d are radially expandable from a compressed or non-deployed state, as shown in FIGS. 9a, 9b, 10a and 10b, to an expanded or deployed state, as depicted in FIGS. 9c, 9d, 10c and 10d.

In one embodiment, as can be understood from FIGS. 9a-10d, each cell 120 includes an upper primary member or strut 115 and a lower primary member or strut 115. The two primary struts 115 join to each other at a single end such that, when the stent 100 is expanded, the primary struts 115 of a cell 120 form a V-shape, wherein the open end 155 and apex 160 of the V-shape coincides with the longitudinal dimension of the stent 100.

In one embodiment, as shown in FIGS. 9a, 9c, 10a and 10c, for each cell 120, a first restrainer portion 172 is located on one primary strut 115 at or near the open end 155 of the cell 120, and a second restrainer portion 174 is located on the other primary strut 115 at or near the open end 155 of the cell 120. Additionally, for each cell 120, first and second restrainer portions 172, 174 are located at or near the apex 160 of the cell 120. As can be understood from FIGS. 9a and 10a, the restrainer portions 172, 174 at the open end 155 of a cell 120 will mate with each other, and the restrainer portions 172, 174 at the apex 160 of a cell 120 will mate with the restrainer portions 172, 174 at the apexes 160 of the immediately adjacent cells 120.

As shown in FIGS. 9a and 10a, in one embodiment, the restrainer portions 172, 174 mechanically engage each other to form a restrainer 126 that maintains the associated primary struts 115 adjacent each other, which thereby keeps the associated cell 120 compressed and the stent 100 in the non-deployed state. As indicated in FIGS. 9c and 10c, the restrainer portions 172, 174 can be disengaged from each other to allow the associated primary struts 115 to move away from each other, which allows the associated cell 120 to expand and the stent 100 to assume a deployed state. In one embodiment, the restrainer portions 172, 174 can be coupled to each other and recoupled to each other, as well as decoupled.

In one embodiment, as illustrated in FIGS. 9a-9d, one restrainer portion 172 has a groove portion 180 and a lip 182, and the other restrainer portion 174 has an arm 184 with a finger, latch tab 186 that is received in the groove 180 and retained therein by engagement with the lip 182. When the tab 186 is being forced into being received in the groove 180 (e.g., when the stent 100 is being compressed into the non-deployed state), the arm 184 deflects to allow the tab 186 to clear the lip 182 and be received in the groove 180, thereby forming a restrainer 126 to maintain the stent 100 in the non-deployed state. When the stent 100 is subjected to an expanding force (e.g., via the expansion of a balloon located within the stent 100), the lever arm 184 deflects to allow the tab 186 to clear the lip 182, thereby causing the restrainer 126 to fail or release and the stent 100 to expand to the deployed state. More specifically, because the mating surfaces of the lip 182 and tab 186 are inclined to the longitudinal axis of the stent 100, an internal expansion force provided by balloon inflation applies a hoop stress to the ramped surfaces, thereby causing the arm 184 to deflect away from the lip 182 until the tab 186 clears lip 182. Thus, the restrainer 126 fails or releases, and the stent 100 is free to expand.

In one embodiment, as illustrated in FIGS. 10a-10d, one restrainer portion 172 is a female portion 172 for receiving another restrainer portion 174, which is a male portion 174. In one embodiment, as shown in FIGS. 10a-10d, the female and male portions 172, 174 are rounded and include slots 127 to assist the restrainer portions 122, 124 in deforming while coupling together or decoupling.

In one embodiment, the mechanical coupling arrangements between the restrainer portions 172, 174 depicted in FIGS. 9a-10d are replaced with bonded arrangements as discussed with respect to FIGS. 4a-4e, 6a-6d and 8a-8d. In other words, the restrainer portions 172, 174 are bonded to each other to form a restrainer 126 that maintains the associated primary struts 115 adjacent each other, which thereby keeps the associated cell 120 compressed and the stent 100 in the non-deployed state. In one embodiment, the restrainer portions 172, 174 have a bond that is formed via sonic welding, heat welding, chemical welding, or mechanical welding. Alternatively, in one embodiment, the bond is an uninterrupted integral extension of one restrainer portion 172 to the other restrainer portion 174, thereby forming the restrainer 126. The restrainer portions 172, 174 are disengaged from each other by causing the bond to fail, thereby allowing the associated primary struts 115 to move away from each other, which allows the associated cell 120 to expand and the stent 100 to assume a deployed state.

As shown in FIGS. 9a and 10a, when the stent 100 is in the compressed or non-deployed state, the struts 115 are positioned close to each other. More specifically, in one embodiment, when the stent 100 is in the compressed or non-deployed state, the struts 115 are oriented generally parallel to each other. As indicated in FIGS. 9b and 10b, when the stent 100 is in the compressed or non-deployed state, the radius of the curvature of the wall 110 is small.

As shown in FIGS. 9c and 10c, when the stent 100 is in the expanded or deployed state, the struts 115 are positioned away from each other. More specifically, in one embodiment, when the stent 100 is in the expanded or deployed state, the primary struts 115 are displaced away from each other near the open end 155 of the cell 120, but remain adjacent to each other where the struts 115 join to form the apex 160 of the cell, thereby forming a V-shaped expanded cell 120. In one embodiment, when the stent 100 is in the expanded or deployed state, the primary struts 115 displace from each other to form an expanded serpentine or zigzag shape with acute angles σ between the pairs of struts 115 at the joining or apex 160 of the struts 115. In one embodiment, as indicated in FIGS. 9d and 10d, when the stent 100 is in the compressed or non-deployed state, the radius of the curvature of the wall 110 is large.

Figure 11A:
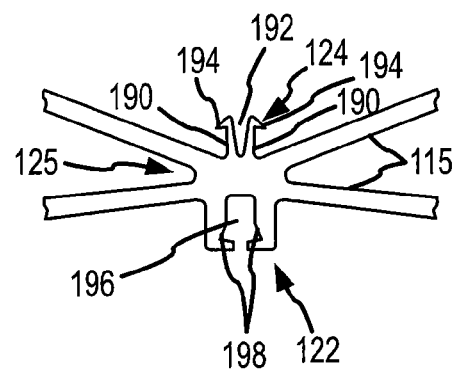
FIG. 11a is a side elevation of a cell interconnection similar to that depicted in FIG. 3c, except employing an alternative embodiment of the female and male restrainer portions.
Figure 12A:
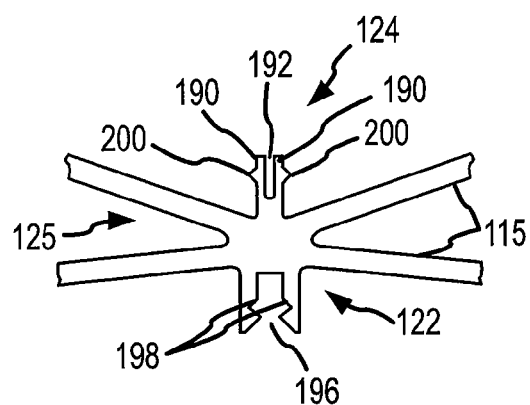
FIG. 12a is a side elevation of a cell interconnection similar to that depicted in FIG. 3c, except employing an alternative embodiment of the female and male restrainer portions.
Figure 12B:
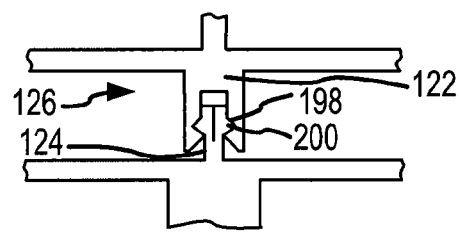
FIG. 12b is a side elevation of the male restrainer portion of FIG. 12a being received in the female restrainer portion.

For a discussion of alternative embodiments of a female/male restrainer 126 that can be employed in place of the female/male restrainers 126 illustrated in FIGS. 3a-3d, 5a-5d, 7a-7d and 10a-10d, reference is made to FIGS. 11a-11b and 12a-12b. FIG. 11a is a side elevation of a cell interconnection 125 similar to that depicted in FIG. 3c, except employing an alternative embodiment of the female and male restrainer portions 122, 124. FIG. 11b is a side elevation of the male restrainer portion 124 of FIG. 11a being received in the female restrainer portion 122. FIG. 12a is a side elevation of a cell interconnection 125 similar to that depicted in FIG. 3c, except employing an alternative embodiment of the female and male restrainer portions 122, 124. FIG. 12b is a side elevation of the male restrainer portion 124 of FIG. 12a being received in the female restrainer portion 122.

As illustrated in FIG. 11a, the male restrainer portion 124 includes a pair of extensions 190 separated by a gap 192 and each terminating in tangs 194. The female restrainer portion 122 includes a slot 196 having therein a pair of angle-surfaced recesses 198. As shown in FIG. 11b, when the female and male restrainer portions 122, 124 are coupled together, the extensions 190 are received in the slot 196 such that the tangs 194 nest in the angle-surfaced recesses 198. The gap 192 in the male restrainer portion 124 allows the male restrainer portion 124 to resiliently deflect in order to be received in the gap 192 or to allow the male restrainer portion 124 to exit the gap 192 when an expanding force is applied to the stent 100 (e.g., via the expansion of a balloon located within the stent 100).

As illustrated in FIG. 12a, the male restrainer portion 124 includes a pair of extensions 190 separated by a gap 192 and each having angle-surfaced protrusion 200 thereon. The female restrainer portion 122 includes a slot 196 having therein a pair of angle-surfaced recesses 198. As shown in FIG. 12b, when the female and male restrainer portions 122, 124 are coupled together, the extensions 190 are received in the slot 196 such that the angle-surfaced protrusions 200 nest in the angle-surfaced recesses 198. The gap 192 in the male restrainer portion 124 allows the male restrainer portion 124 to resiliently deflect in order to be received in the gap 192 or to allow the male restrainer portion 124 to exit the gap 192 when an expanding force is applied to the stent 100 (e.g., via the expansion of a balloon located within the stent 100).

As can be understood from FIGS. 3a-3d, 5a-5d, 7a-7d, 9a-9d, 10a-10d and 11a-12b, in one embodiment, each pair of male and female restrainer portions 122, 124 are integral to a cell 120 and can reversibly couple to one another by application of an external compressive force. An external compressive force acting to reduce the circumference of an expanded stent causes the male and female restrainer portion 122, 124 to deform until the portions 122, 124 are joined mechanically. As previously mentioned, in some embodiments, one or both restrainer portions 122, 124 will have slots 127, 192. Where a male restrainer portion 124 is provided with a slot 127, 192, the slot 127, 192 will allow the male restrainer portion 124 to compress to be received within the female restrainer portion 122. Where a female portion 122 is provided with a slot 127, the slot 127 will allow the female restrainer portion 122 to expand to receive the male restrainer portion 124. Once the external compressive force is removed from the stent 100, the coupled restrainer portions 122, 124, which are integral to the stent 100, will have sufficient resistance to uncoupling that the stent 100 is held in the compressed or non-deployed state securely about the balloon of a balloon catheter.

While various strut 115, 150 and restrainer 126 configurations have been depicted in FIGS. 3a-12b, those skilled in the art will understand that other strut 115, 150 and restrainer 126 configurations can be employed without departing from the scope of the present invention. For example, the serpentine strut pattern depicted in U.S. Pat. No. 6,893,458 to Cox et al., which issued May 17, 2005 and is hereby incorporated by reference in it entirety, could be provided with any of the previously described integral restrainers 126 to maintain the stent 100 in a non-deployed state until an expanding force causes the restrainers 126 to fail or release, thereby allowing the stent 100 to expand to a deployed state. Because of the applicability of the inventive concepts of the present invention, the present invention should not be construed as being limited in the types of strut 115, 150 or restrainer 126 configurations that may employed by the present invention.

In one embodiment, the restrainers 126 are integrally formed in the stent 100 in the same manner used to form the stent struts 115, 150. For example, in one embodiment the restrainers 126 are formed by laser cutting a thin wall metal tube (e.g., stainless steel, Nitinol, etc.). In one embodiment, the restrainers 126 are formed by acid etching a thin wall metal tube. In one embodiment, the restrainers 126 are formed by laser cutting or acid etching a thin flat metal sheet, forming the sheet into a cylinder and then welding the cylinder in the longitudinal direction.

The mechanical coupling of the restrainer portions 122, 124, 172, 174 of the restrainers 126 can be caused to uncouple by increased hoop stress in the stent 100 developed by expansion of the balloon about which the stent 100 is mounted. When increasing balloon pressure is applied to the stent 100, the hoop stress on the restrainer portions 122, 124, 172, 174 increases until sufficient deformation occurs to cause the restrainers 126 to release and allow the stent 100 to expand.

In one embodiment of the stent 100, the mechanical coupling configurations or bonds 128 employed by restrainer portion 122, 124, 172, 174 are selectively sized to allow a selected portion of the stent 100 to expand prior to another portion of the stent 100. In other words, by controlling the mechanical fit or the bond strength, as the case may be, between the various restrainer portions 122, 124, 172, 174, a first portion of the stent can be caused to expand prior to another portion of the stent 100. For example, in one embodiment, the two stent ends are allowed to expand prior to the middle of the stent 100. Alternatively the middle of the stent 100 is allowed to expand prior to the ends of the stent 100. This staged expansion of the stent 100 allows the stent 100 to expand in a controlled fashion to eliminate stent jumping that can lead to inaccurate placement. Specifically, the staged expansion controls the total forces acting on the stent 100 to neutralize unbalanced forces that can cause the stent 100 to move axially from the desired position.

In embodiments where the stent ends are to be deployed first, the strength of the mechanical fit or bond 128 between the restrainer portions 122, 124, 172, 174 is lower at the ends of the stent 100 than the strength of the mechanical fit or bond 128 of the restrainer portions 122, 124, 172, 174 at the middle of the stent 100. In embodiments where the stent middle is to be deployed first, the strength of the mechanical fit or bond 128 between the restrainer portions 122, 124, 172, 174 at the middle of the stent 100 is lower than the strength of the mechanical fit or bond 128 of the restrainer portions 122, 124, 172, 174 at the ends of the stent 100. By staging the deployment of the stent 100 in such a manner, the various methods of restraining the stent contemplated in the prior art are no longer necessary. Accordingly, as compared to the prior art, the stent 100 and its deployment system are less complicated to use, have smaller diameters, and are more readily negotiable through the vasculature of a patient.

In one embodiment, to modify or control the strength of the mechanical coupling between the female and male restrainer portions 122, 124, 172, 174 of a selected portion of the stent 100 to allow the selected stent portion to expand prior to another stent portion, the strength of the mechanical coupling is reduced. For example, in one embodiment, the restrainer portions 122, 124, 172, 174 in the selected stent portion are heat, mechanically or chemically treated to have a reduced stiffness and be more readily able to release or fail. In one embodiment, the restrainer portions 122, 124, 172, 174 in the selected stent portion are formed with reduced engagement surfaces between the male and female restrainer portions 122, 124, 172, 174 such that the engagement surfaces offer less ability to withstand an expansion force provided by a balloon.

In one embodiment, to modify or control the strength of the bonds 128 of a selected portion of the stent 100 to allow the selected stent portion to expand prior to another stent portion, the strength of the bonds 128 is altered by reducing the cross-section of the bond 128 by notching the bond 128 at it's minimum cross-section. In one embodiment, the strength of the bonds 128 is altered by thinning or chemically attacking the bond 128 at it's weakest point.

In one embodiment, the thickness of the stent wall 110 is typically 0.003-0.005" thick for small stents 100 (e.g., stents 100 used in coronary arteries) and up to 0.006-0.009" thick for larger diameter stents 100 (e.g., stents 100 used in carotid or peripheral arteries). Since the thickness of the stent wall 110 is small, in one embodiment, the wall draft angles of the restrainer portions 122, 124, 172, 174 need to be controlled to prevent the radial passing of the male restrainer portion 124, 174 through the female restrainer portion 122, 172 (or vice versa). So controlling the fit between the restrainer portions 122, 124, 172, 174 prevents the restrainer portions 122, 124, 172, 174 from decoupling except upon being subject to circumferential hoop forces that exceed the coupling strength of the restrainers 126. As a result, forces exerted on the stent 100 due to the stent 100 encountering bends in an artery when tracking the artery do not cause the stent 100 to deploy inadvertently.

In one embodiment, the sizing or controlling of the fit between the restrainer portions 122, 124, 172, 174 is accomplished by initial stent cutting or etching. Alternatively, the sizing or controlling of the fit between the restrainer portions 122, 124, 172, 174 is accomplished by subsequent metal working operations well known in the art. As can be understood from FIGS. 11a-12b, in one embodiment, the restrainer portions 122, 124 are laser cut, which leaves a gap or space between the female and male portions 122, 124 when the male portion 124 is received in the female portion 122. The space or gap can be altered by expanding the diameter of the slit or gap 192 in the male portion 124 and shaping the stent wall 110 of the male portion 124 in a tapered fashion to interlock with the mating female portion 122.

As previously mentioned, in one embodiment of the stent 100, the restrainers 126 include male and female portions 122, 124 that reversibly interlock or couple circumferentially upon application of an external force. These portions 122, 124 also uncouple upon application of sufficient balloon pressure, thereby allowing the stent 100 to expand or deploy.

Although every cell 120 in the embodiments depicted in FIGS. 3a-10d is shown with a restrainer 126, it should be understood that, in other embodiments, some cells 120 will have restrainers 126 and other cells 120 will not have restrainers 126. For example, in one embodiment of a self-expandable stent 100, a substantial number, or even all, of the cells 120 will have a restrainer 126 for resisting the self-expanding force of the stent 100. For balloon expandable stents 100, a substantially smaller number of cells 120 will have restrainers 126 as a balloon expandable stent 100 typically offers little of its own expansion force. For example, in one embodiment of a balloon expandable stent 100, one or two longitudinally offset circumferential rings 130 of restrainer 126 equipped cells 120 would likely be sufficient to retain the stent 100 in a compressed or non-deployed state about the balloon 320. In one embodiment, a balloon expandable stent 100 is maintained in the compressed or non-deployed state by a few restrainer 126 equipped cells 120 selectively located about the balloon expandable stent 100 (e.g., the restrainers 126 are located about or next to the inner lumen marker bands of a balloon catheter, which greatly aids in the retention of balloon expandable stents 100).

Figure 13:
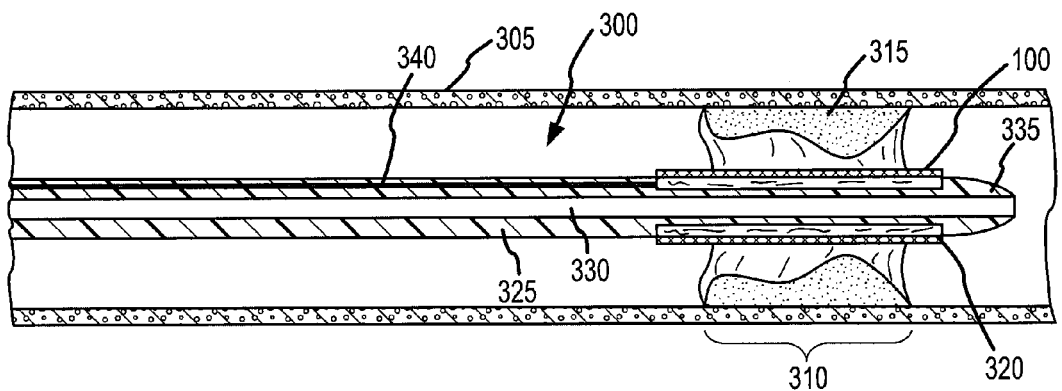
FIG. 13 is a longitudinal cross-section of a balloon catheter with a stent mounted thereon in a compressed or non-deployed state, wherein the catheter extends through a body lumen (e.g., a coronary or carotid artery) and the stent is positioned in a treatment area partially occluded by a stenosis formed by atherosclerotic plaque.
Figure 14:
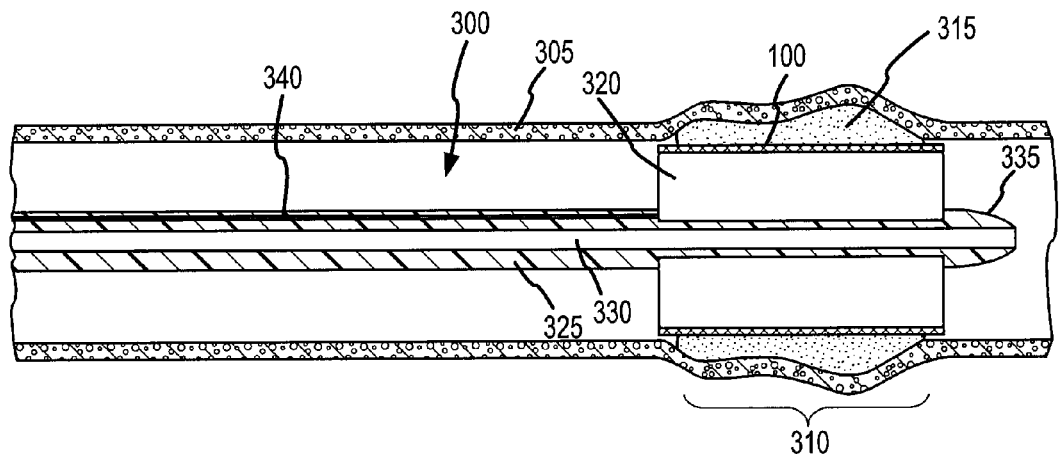
FIG. 14 is the same view depicted in FIG. 13, except the balloon has been inflated to fully expand or deploy the stent, thereby displacing the atherosclerotic plaque of the stenosis.
Figure 15:
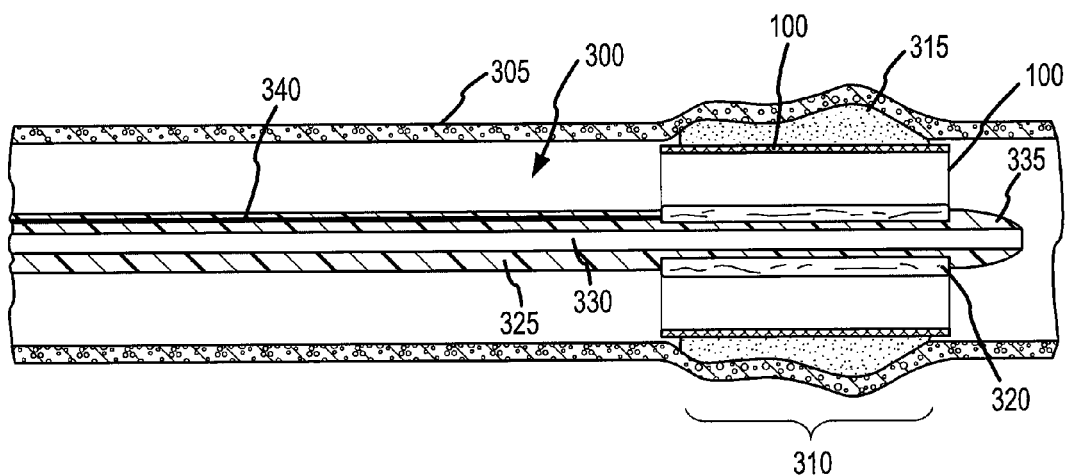
FIG. 15 is the same view depicted in FIG. 14, except the balloon has been deflated to allow the catheter's withdrawal from the fully deployed stent.
Figure 16:
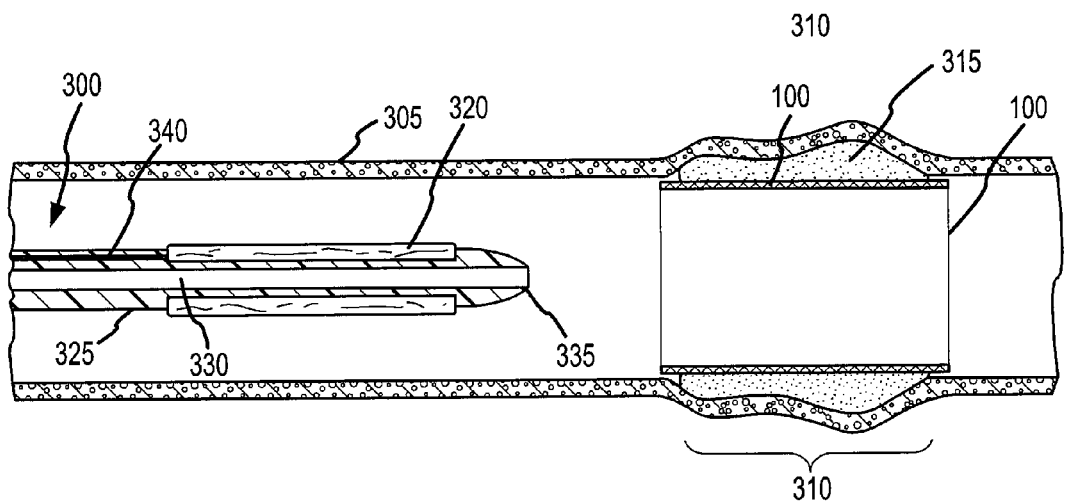
FIG. 16 is the same view depicted in FIG. 15, except the catheter has been withdrawn from the fully deployed stent.
Figure 17:
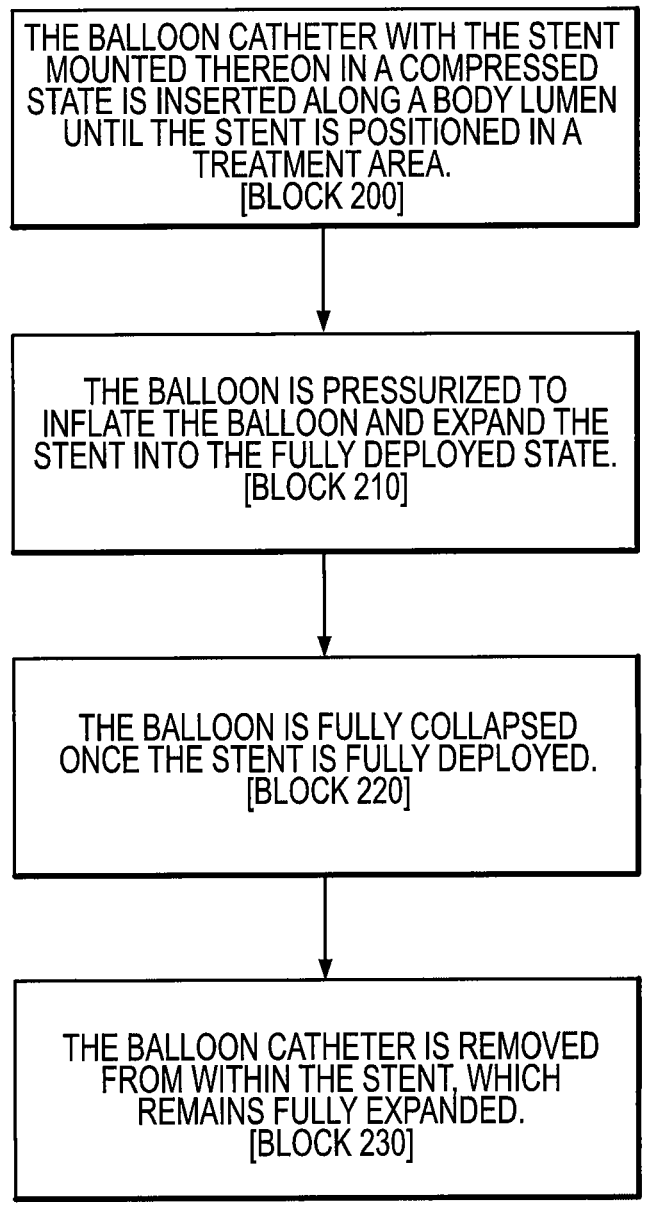
FIG. 17 is a flow diagram indicating the steps comprising the method of the subject invention.

For a discussion of one embodiment of a method of deploying the stent 100, reference is now made to FIGS. 13-16 and 17. FIG. 13 is a longitudinal cross-section of the balloon catheter 300 with the stent 100 mounted thereon in a compressed or non-deployed state, wherein the catheter 300 extends through a body lumen (e.g., a coronary or carotid artery) 305 and the stent is positioned in a treatment area 310 partially occluded by a stenosis 315. FIG. 14 is the same view depicted in FIG. 13, except the balloon 320 has been inflated to expand and deploy the stent 100, thereby compressing the atherosclerotic plaque of the stenosis 315. FIG. 15 is the same view depicted in FIG. 13, except the balloon 320 has been deflated to allow the catheter's withdrawal from the fully deployed stent 100. FIG. 16 is the same view depicted in FIG. 15, except the catheter 300 has been withdrawn from the fully deployed stent 100. FIG. 17 is a flow diagram indicating the steps comprising the method of the subject invention.

As indicated in FIG. 13, the balloon catheter 300 includes a tubular body 325, a central or guidewire lumen 330 extending through the body 325, a balloon 320 located near a distal end 335 of the body 325, an inflation lumen 340 extending through the body 325 and in fluid communication with the balloon 320, and a stent 100 located about the balloon 320. As indicated in FIGS. 13 and 17, the balloon catheter 300, with the stent 100 mounted thereon in a compressed or non-deployed state about the balloon 320, is inserted along a body lumen 305 until the stent 100 is positioned in a treatment area 310 [block 200]. The stent 100 may have any one of the strut configurations and may employ any one or more of the aforementioned restrainers 126 to maintain the stent 100 in a compressed or non-deployed state about the balloon 320.

As illustrated in FIGS. 14 and 17, the balloon 320 is pressurized to inflate the balloon 320, thereby subjecting the stent 100 to a hoop stress, which when sufficiently large, causes the restrains 126 to fail or release. In the case of a self-expanding stent 100, once the restrainers 126 have been overcome by the initial expansion of the balloon 320, the stent 100 is free to self-expand on its own to its fully expanded or deployed state. In the case of a balloon expanded stent 100, once the restrainers 126 have been overcome by the initial expansion of the balloon 320, the stent 100 is free to be expanded to its fully expanded or deployed state via further expansion of the balloon 320 [block 210]. Full expansion of the stent 100 radially displaces the atherosclerotic plaque of the stenosis 315, thereby eliminating or significantly reducing the occlusion caused by the stenosis 315. Once the balloon 320 is fully expanded, as depicted in FIG. 14, the balloon 320 can be fully expanded to apply post dilation of the stent 100.

As shown in FIGS. 15 and 17, once the stent 100 is fully expanded or deployed, whether for initial expansion of the stent 100 or for post dilation of the stent 100, the balloon 320 is fully collapsed to allow the removal of the balloon catheter 300 from the stent 100 [block 220]. The stent 100 remains fully deployed or expanded although the balloon catheter 300 has been removed from the stent 100. The stent 100 remains fully deployed or expanded because it is biased towards full expansion due to its physical configuration (e.g., the balloon 320 has plastically deformed the stent 100, which was a balloon deployed stent 100, or the stent 100 is a self-expanding stent 100). In one embodiment, the balloon 320 is re-expanded to provide post dilation of the stent 100 and stenosis 315.

As illustrated in FIGS. 16 and 17, the balloon catheter 300 is removed from within the stent 100, which is fully expanded [block 230]. The stent 100 now maintains the stenosis 315 against the inner wall of the body lumen 305 to significantly reduce the occlusion of the body lumen 305.

As can be understood from the preceding discussion, in its various embodiments, the stent 100 and its method of deployment are advantageous for several reasons. For example, because of the subject invention, a self-expanding type stent 100 can be deployed without having to be restrained by a sheath extending about the stent 100. Consequently, a catheter exchange, as required by the prior art for self-expanding stents, can be eliminated, thereby reducing procedure complexity and time requirements. Furthermore, trackability for the stent 100 and its deployment system is superior to prior art stents and deployment systems because the present invention offers reduced delivery system bulk and profile. By selectively controlling the release or failure capability of restrainers 126 on selected portions of the stent 100, the stent 100 can be expanded in a controlled fashion with improved accuracy and without taking additional steps or providing additional equipment to prevent the stent 100 from jumping during delivery.

Although various embodiments of this invention have been described above with a certain degree of particularity or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments, and not limiting. Changes in detail or structure may be made without departing from the basic elements of the invention as defined in the following claims.

What is claimed is:

1. A vascular stent without an outer sheath or sleeve extending about the stent during delivery or use, the stent comprising:
    a cylindrical wall radially expandable from a compressed state to an expanded state, with an outer sheath or sleeve extending about the all of the stent during delivery or use, and including a plurality of cells, at least one cell including a first primary member having a first integral restrainer member and a second primary member having a second integral restrainer member,
    wherein, when the cylindrical wall is in the expanded state, the first and second primary members are located a greater distance from each other than when the cylindrical wall is in the compressed state,
    wherein the first restrainer member includes a rounded male restrainer portion and the second restrainer member includes a rounded female restrainer portion configured to receive the rounded male portion, and the first and second restrainer members join by insertion of the rounded male restrainer portion through an inlet opening of the rounded female restrainer portion in a direction of movement of the first and second primary members relative to each other to maintain the cylindrical wall in the compressed state;
    wherein the rounded male restrainer portion and the rounded female restrainer portion each include a slot to assist the restrainer portions in deforming while coupling together or while decoupling,
    wherein an expansion force applied to the cylindrical wall causes the first and second restrainer members to separate, thereby freeing the cylindrical wall to expand from the compressed state to the expanded state,
    wherein the vascular stent is formed around a balloon catheter and the expansion force is the inflation of a balloon of the balloon catheter.

2. The stent of claim 1, wherein the first primary member includes a first end joining a first end of the second primary member and a second end joining a second end of the second primary member.

3. The stent of claim 2, wherein the first and second primary members deflect near their respective longitudinal centers when the cylindrical wall expands from the compressed state to the expanded state.

4. The stent of claim 3, wherein the first and second restrainer members are located near the longitudinal centers of their respective primary members.

5. The stent of claim 1, wherein each primary member includes first and second ends and wherein said at least one cell further includes a first pair of intermediate members extending between the first ends of the primary members and a second pair of intermediate members extending between the second ends of the primary members.

6. The stent of claim 5, wherein the primary and intermediate members are oriented generally parallel to each other when the cylindrical wall is in the compressed state.

7. The stent of claim 6, wherein the primary members are oriented generally parallel to each other and the intermediate members are generally nonparallel to the primary members when the cylindrical wall is in the expanded state.

8. The stent of claim 7, wherein the intermediate members form an acute angle with the immediately adjacent primary member when the cylindrical wall is in the expanded state.

9. The stent of claim 1, wherein the first primary member includes a first end joining a first end of the second primary member and a second end displaceable from a second end of the second primary member.

10. The stent of claim 1, in which the first restrainer member mechanically engages the second restrainer member.

11. The stent of claim 1, wherein the stent is generally self-expanding once the first and second restrainer members separate.

12. The stent of claim 1, wherein the stent generally requires the application of an expanding force to fully expand the stent once the first and second restrainer members separate.

13. The vascular stent of claim 1, wherein the restrainer members on a first portion of the stent are adapted to fail or release prior to the restrainer members on a second portion of the stent.

14. A system for deploying a vascular stent without an outer sheath or sleeve extending about the stent during delivery or use, the system comprising:
    a catheter including a balloon at a distal end of the catheter; and
    a radially expandable stent extending about the balloon and including a plurality of integral restrainer members maintaining the stent in a collapsed state, without an outer sheath or sleeve extending about the stent during delivery or use, and
    wherein expanding the balloon causes the restrainer members to release, thereby allowing the stent to expand and
    wherein each restrainer member includes a first mechanical engagement feature and a second mechanical coupling engagement feature, each feature being an integrally formed part of the stent and
    wherein the first mechanical engagement feature includes a rounded male portion and the second mechanical coupling engagement feature includes a rounded female portion having a receiving cavity configured to receive the male restrainer portion in a direction of movement of the stent between expanded and collapsed states to maintain the stent in the collapsed state, and wherein the rounded male restrainer portion and the rounded female restrainer portion each include a slot to assist the restrainer portions in deforming while coupling together or decoupling, the slot of the rounded female portion being separate from the receiving cavity.

15. The system of claim 14, wherein first mechanical engagement feature separates from the second mechanical engagement feature when the restrainer member is caused to release via the balloon expansion.

16. The system of claim 14, wherein the stent is generally self-expanding once the restrainer members separate.

17. The system of claim 14, wherein the stent generally requires
   further expansion of the balloon to fully expand the stent once the restrainer members separate.

18. The system of claim 14, wherein the restrainer members on a first portion of the stent are adapted to release prior to the restrainer members on a second portion of the stent.

19. A stent deploying system comprising:
   a balloon catheter including a tubular body and a balloon coupled to the tubular body near a distal end of the tubular body; and
   a vascular stent on the balloon, the stent including a restrainer member that is integral to the stent and acts to hold the stent in a collapsed state without an outer sheath or sleeve extending about the stent during delivery or use,
   wherein the restrainer member includes a first rounded coupling member on a first strut and a second rounded coupling member on a second strut, the second rounded coupling member having a receiving cavity sized to receive the first rounded coupling member, the coupling members interacting to mechanically couple the first and second struts and each coupling member including a slot to assist the coupling member in deforming while coupling together, the slot of second rounded coupling member being separate from the receiving cavity, and
   wherein when the balloon is caused to expand, the ability of the restrainer member to hold the stent in the collapsed state is overcome and the stent is free to expand.

20. The system of claim 19, wherein the coupling members decouple upon expansion of the balloon.

21. A radially expandable stent comprising a plurality of restrainer members that are integral to the stent and adapted to maintain the stent in a compressed state without an outer sheath or sleeve extending about the stent during delivery or use, wherein the restrainer members on a first portion of the stent are adapted to release prior to the restrainer members on a second portion of the stent and wherein each restrainer member includes a rounded female portion with a slot and a rounded male portion with a slot, the female portion having a receiving cavity with an opening facing the male portion and configured to receive the male portion to maintain the stent in a compressed state and the slots configured to assist the respective portion in increasing or decreasing in size while coupling together.

22. The stent of claim 21, wherein the first portion is a middle portion of the stent and the second portion is an end portion of the stent.

23. The stent of claim 21, wherein the first portion is an end portion of the stent and the second portion is middle portion of the stent.

* * * * *